(12) United States Patent
Baverel et al.

(10) Patent No.: US 11,324,743 B2
(45) Date of Patent: May 10, 2022

(54) TREATMENT FOR THE NON ALCOHOLIC STEATOHEPATITIS AND FIBROSIS

(71) Applicant: METABOLYS, Lyons (FR)

(72) Inventors: Gabriel Baverel, Saint Cyr Au Mont d'Or (FR); Gérard Moinet, Orsay (FR)

(73) Assignee: METABOLYS, Lyons (FR)

( * ) Notice: Subject to any disclaimer, the term of this patent is extended or adjusted under 35 U.S.C. 154(b) by 0 days.

(21) Appl. No.: 16/323,094

(22) PCT Filed: Aug. 3, 2017

(86) PCT No.: PCT/EP2017/069595
§ 371 (c)(1),
(2) Date: Feb. 4, 2019

(87) PCT Pub. No.: WO2018/024805
PCT Pub. Date: Feb. 8, 2018

(65) Prior Publication Data
US 2019/0160057 A1    May 30, 2019

(30) Foreign Application Priority Data
Aug. 4, 2016  (EP) ................................. 16306010

(51) Int. Cl.
*A61K 31/496* (2006.01)
*A61K 31/495* (2006.01)
*A61P 1/16* (2006.01)

(52) U.S. Cl.
CPC .......... *A61K 31/496* (2013.01); *A61K 31/495* (2013.01); *A61P 1/16* (2018.01)

(58) Field of Classification Search
CPC combination set(s) only.
See application file for complete search history.

(56) References Cited

U.S. PATENT DOCUMENTS

| | | |
|---|---|---|
| 8,217,046 B2 | 7/2012 | Perez et al. |
| 8,513,258 B2 | 8/2013 | Perez et al. |
| 9,133,073 B2 | 9/2015 | Sharma |
| 9,150,523 B2 | 10/2015 | Moinet et al. |
| 9,150,529 B2 | 10/2015 | Moinet et al. |
| 9,545,387 B2 | 1/2017 | Moinet et al. |
| 2008/0194575 A1 | 8/2008 | Beraza et al. |
| 2009/0176803 A1 | 7/2009 | Perez et al. |
| 2011/0082119 A1 | 4/2011 | Yano |
| 2012/0232097 A1 | 9/2012 | Perez et al. |
| 2013/0066075 A1 | 3/2013 | Shibata et al. |
| 2014/0155409 A1 | 6/2014 | Moinet et al. |
| 2014/0221390 A1 | 8/2014 | Shibata et al. |
| 2014/0235650 A1 | 8/2014 | Moinet et al. |

FOREIGN PATENT DOCUMENTS

EP 2573081 3/2013

OTHER PUBLICATIONS

Loomba (Association between diabetes, family history of diabetes and risk of nonalcoholic steatohepatitis and fibrosis, Hepatology, Sep. 2012; 56(3), p. 943-951).*
Shahinul Alam et al: 11 Effect of telmisartan on histological activity and fibrosis of non-alcoholic steatohepatitis: A 1-year randomized control trial 11, Saudi Journal of Gastroenterology, vol. 22, No. 1, Jan. 1, 2016 (Jan. 1, 2016), p. 69, XP055333534, ISSN: 1319-3767, DOI: 10.4103/1319-3767.173762 abstract.
Internatinoal Search Report for PCT/EP2017/069595, dated Oct. 10, 2017.
Written Opinion of the International Searching Authority for PCT/EP2017/069595, dated Oct. 10, 2017.
European Search Report for EP 16306010, dated Jan. 10, 2017.
Loomba, et al, "Association Between Diabetes, Family History of Diabetes, and Risk of Nonalcoholic Steatohepatitis and Fibrosis", Sep. 2012, pp. 943-951, vol. 56, No. 3, Hepatology.
Loomba, et al, "Association between diabetes, family history of diabetes and risk of nonalcoholic steatohepatitis and fibrosis", Sep. 2012, pp. 943-951, vol. 56, issue 3, Hepatology.
Alam, et al, "Effect of Telmisartan on Histological Activity and Fibrosis of Non-alcoholic Steatohepatitis: A 1-Year Randomized Control Trial", Jan. 2016, pp. 69-76, vol. 22, No. 1, The Saudi Journal of Gastroenterology.
Zhulenko, et al, "Manuals and Tutorials for Students Institutions of Higher Education", Veterinary textbook, 2008.
Kharkevich, DA, Manual relating to treatment and prophylaxis of osteoporosis, 2010.
Belikov, Pharmacy textbook, 2001.

* cited by examiner

*Primary Examiner* — Kathrien A Cruz
(74) *Attorney, Agent, or Firm* — B. Aaron Schulman, Esq.; Stites & Harbison, PLLC

(57) ABSTRACT

Compounds of formula (I) or their enantiomers, diastereoisomers thereof and the addition salts thereof with pharmaceutically acceptable bases or acids, for use for the prevention or treatment, preferably treatment, of NASH.

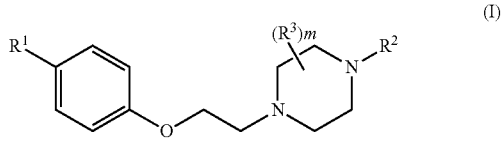

13 Claims, 3 Drawing Sheets

TREATMENT FOR THE NON ALCOHOLIC STEATOHEPATITIS AND FIBROSIS

Figure 1:
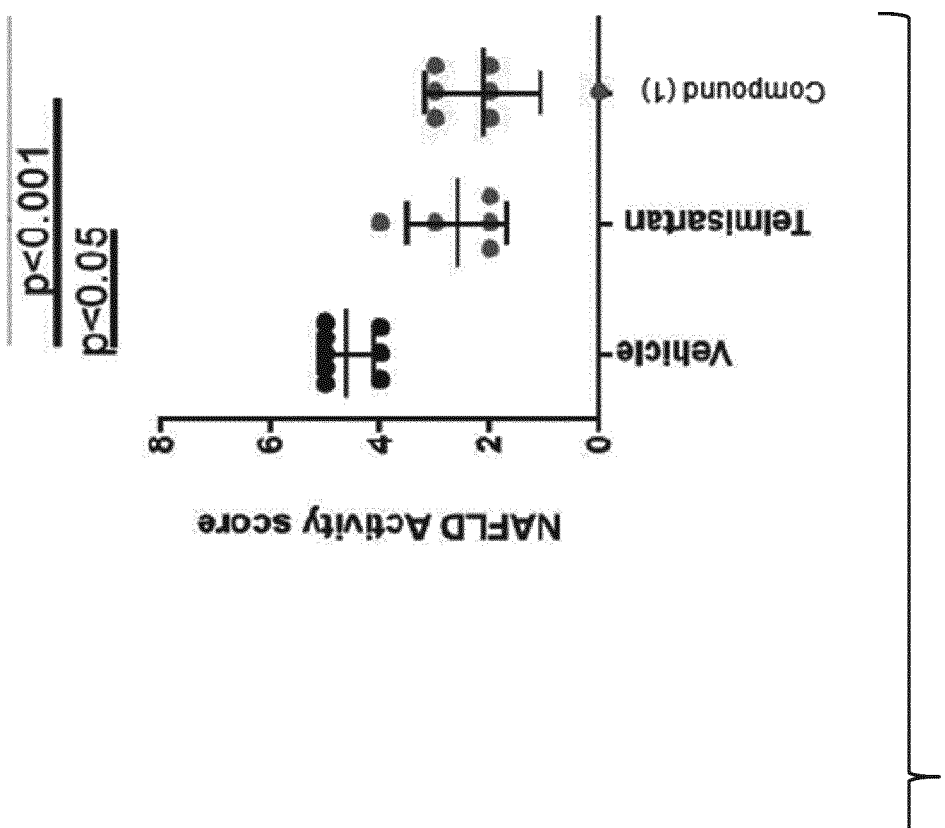
Figure 1:
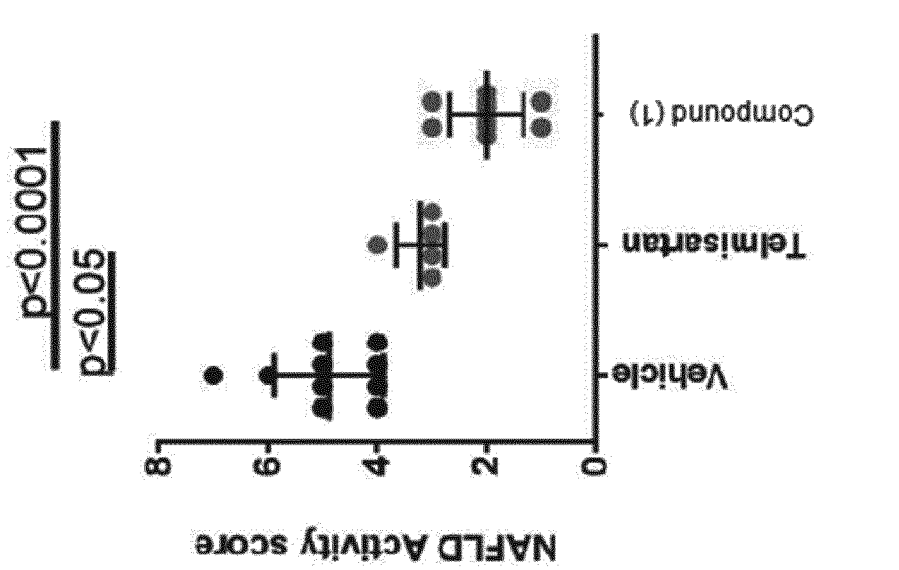

The present invention relates to new treatment for the Non Alcoholic SteatoHepatitis (NASH) and fibrosis.

The Non Alcoholic SteatoHepatitis (NASH) is a liver disease characterized in the liver by: (1) steatosis (fat accumulation), (2) lobular inflammation and (3) destruction of hepatic cells (ballooning). It is part of the group of Non Alcoholic Fatty Liver Diseases (NAFLDs) which begin with hepatic steatosis which is benign but may progress to NASH, fibrosis, cirrhosis with permanent liver damage, hepatocellular carcinoma and death.

NAFLD is often associated with obesity and type 2 diabetes whose prevalences are extremely high and continue to increase worldwide.

In the USA, NASH is estimated to be present in 12% of the adult population and in 22% of diabetic patients. It is also estimated that 15-25% of patients suffering from NASH will develop cirrhosis (liver fibrosis, i.e. excess deposition of fibrous tissue in organs). NASH also considerably increases the risk of cardio-vascular accidents.

Currently, there is no efficacious drug for treating NASH and the health regulatory agencies (FDA, EMA) consider that the management of NASH epidemic is a priority.

There is thus a need to provide efficient treatment for NASH.

It is an object of the present invention to provide compounds suitable for use for the prevention and/or treatment of NASH.

It is also an object of the present invention to provide compounds that may also be suitable for use for the prevention and/or treatment of fibrosis, preferably liver fibrosis.

Yet other objectives will emerge from a reading of the following description of the invention.

The present invention relates to compounds of formula (I)

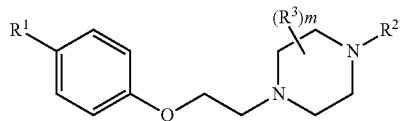

(I)

wherein
$R^1$ represents:
 a group $-C(O)CR^4R^5CR^6R^7C(O)OH$;
 a group $-C(OH)(H)CR^4R^5CR^6R^7C(O)OH$;
 a group

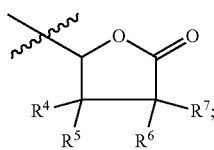

or
 a $-(CH_2)_4C(O)OH$ group;
$m$ represents an integer ranging from 0 to 8;
$R^2$ represents:
 a $C_6$ to $C_{10}$ aryl group optionally substituted; or
 a 5 to 10-membered heteroaryl group optionally substituted;
$R^3$, identical or different, represent:

an alkyl, linear or branched, $C_1$ to $C_5$, preferably $C_1$ to $C_4$; for example methyl, ethyl, propyl, isopropyl, butyl, tert-butyl; optionally substituted by a carbocycle group or by a heterocycle group, the carbocycle being in 5 to 10 members, saturated, partially unsaturated or aromatic, substituted or non-substituted, the heterocycle comprising 5 to 10 members, substituted or non-substituted, saturated, partially unsaturated or aromatic and which may comprise 1, 2 or 3 heteroatoms, identical or different, in particular chosen from nitrogen, oxygen or sulphur, $R^4$, $R^5$, $R^6$ et $R^7$, identical or different, represent:
 a hydrogen atom;
 an alkyl group, linear or branched, in $C_1$ to $C_5$, preferably $C_1$ to $C_4$;
 a 5, 6 or 7-membered carbocycle group saturated, partially insaturated or aromatic, non-substituted or substituted; or
$R^4$ and $R^5$ form together with the carbon atom to which they are bonded a carbocycle with 5, 6 or 7 members, substituted or non-substituted, preferably saturated; for example cyclopentyl or cyclohexyl; or
$R^6$ et $R^7$ form together with the carbon atom to which they are bonded a carbocycle with 5, 6 or 7 members, substituted or non-substituted, preferably saturated; for example cyclopentyl or cyclohexyl;
or their enantiomers, diastereoisomers thereof and the addition salts thereof with pharmaceutically acceptable bases or acids,
for use for the prevention or treatment, preferably treatment, of NASH.

In the present invention "Compound X for use for the treatment of Y" is equivalent to "Compound X for use in a method for the treatment of Y" or "Compound X for use in the therapy of Y".

The term heteroaryl relates to 5 to 10-membered heteroaryl comprising at least one heteroatom, identical or different, chosen among O, N, S, preferably N. The heteroaryl can comprise 1, 2, 3 or 4 heteroatom, identical or different, chosen among O, N, S, preferably N, preferably 1, 2 or 3 heteroatom, identical or different.

The carbocycles, heterocycles, aryl, heteroaryl, are non-substituted or substituted by one or more substituents, identical or different, in particular chosen from:
 a $C_1$ to $C_6$ alkoxy group, linear or branched, for example methoxy, ethoxy, propoxy, isopropoxy, butoxy or tert-butoxy;
 a halogen atom;
 a hydrocarbon group, linear or branched, preferably alkyl, $C_1$ to $C_5$, preferably $C_1$ to $C_4$, for example methyl, ethyl, propyl, butyl, isopropyl, tert-butyl;
 a hydrocarbon group, linear or branched, preferably alkyl, $C_1$ to $C_5$, preferably $C_1$ to $C_4$, substituted in particular by one or more halogen atoms;
 a cyano (—CN) group; or
 a sulfonylalkyl (—S(O)$_2$-alkyl) group, in which the alkyl is linear or branched, $C_1$ to $C_5$, preferably $C_1$ to $C_4$, for example methyl, ethyl, propyl, butyl, isopropyl or tert-butyl;
 a carbocycle group with 5, 6 or 7 members, saturated, partially unsaturated or aromatic, preferably phenyl, substituted or non-substituted, in particular by one or more substituents, identical or different, in particular chosen from a halogen atom, a C1 to C6 alkoxy group, linear or branched, for example methoxy, ethoxy, propoxy, isopropoxy, butoxy or tert-butoxy; an alkyl group, $C_1$ to $C_5$, preferably $C_1$ to $C_4$, for example methyl, ethyl, propyl, butyl, isopropyl or tert-butyl.

Preferably, in the compounds of the present invention m is 0.

Preferably, in the compounds of the invention $R^1$ is —C(O)CH$_2$CH$_2$C(O)OH or —(CH$_2$)$_4$C(O)OH.

Preferably, in the compounds of the invention $R^1$ is —C(O)CH$_2$CH$_2$C(O)OH.

Preferably, in the compounds of the present invention, $R^2$ represents:
- a $C_6$ to $C_{10}$ aryl group optionally substituted by at least a substituent chosen among an $C_1$-$C_6$ alkyl group, linear or branched, or a O—($C_1$-$C_6$)-alkyl group, linear or branched, preferably a O—($C_1$-$C_3$)-alkyl group, linear or branched; or
- a 5 to 10-membered heteroaryl group.

Preferably, in the compounds of the present invention, $R^2$ represents:
- a 5 to 10-membered heteroaryl group.

Preferably, in the compounds of the invention $R^1$ is —C(O)CH$_2$CH$_2$C(O)OH and m is 0.

Preferably, in the compounds of the invention,
m is 0; and
$R^2$ represents:
- a $C_6$ to $C_{10}$ aryl group optionally substituted by at least a substituent chosen among an $C_1$-$C_6$ alkyl group, linear or branched, or a O—($C_1$-$C_6$)-alkyl group, linear or branched, preferably a O—($C_1$-$C_3$)-alkyl group, linear or branched; or
- a 5 to 10-membered heteroaryl group.

Preferably, in the compounds of the invention,
m is 0; and
$R^2$ represents:
- a 5 to 10-membered heteroaryl group.

Preferably, in the compounds of the invention
$R^1$ is —C(O)CH$_2$CH$_2$C(O)OH and
$R^2$ represents:
- a $C_6$ to $C_{10}$ aryl group optionally substituted by at least a substituent chosen among an $C_1$-$C_6$ alkyl group, linear or branched, or a O—($C_1$-$C_6$)-alkyl group, linear or branched, preferably a O—($C_1$-$C_3$)-alkyl group, linear or branched; or
- a 5 to 10-membered heteroaryl group.

Preferably, in the compounds of the invention
$R^1$ is —C(O)CH$_2$CH$_2$C(O)OH and
$R^2$ represents:
- a 5 to 10-membered heteroaryl group.

Preferably, in the compounds of the invention
$R^1$ is —C(O)CH$_2$CH$_2$C(O)OH
m is 0 and
$R^2$ represents:
- a $C_6$ to $C_{10}$ aryl group optionally substituted by at least a substituent chosen among an $C_1$-$C_6$ alkyl group, linear or branched, or a O—($C_1$-$C_6$)-alkyl group, linear or branched, preferably a O—($C_1$-$C_3$)-alkyl group, linear or branched; or
- a 5 to 10-membered heteroaryl group.

Preferably, in the compounds of the invention
$R^1$ is —C(O)CH$_2$CH$_2$C(O)OH
m is 0 and
- a 5 to 10-membered heteroaryl group.

Preferably, in the compounds of the present invention, $R^2$ represents:
- a phenyl group optionally substituted by at least a substituent chosen among an $C_1$-$C_6$ alkyl group, linear or branched, or a O—($C_1$-$C_6$)-alkyl group, linear or branched, preferably a O—($C_1$-$C_3$)-alkyl group, linear or branched; or
- a 6-membered heteroaryl group, preferably comprising at least one nitrogen, preferably pyridine.

Preferably, in the compounds of the present invention, $R^2$ represents:
- a 6-membered heteroaryl group, preferably comprising at least one nitrogen, preferably pyridine.

Preferably, in the compounds of the invention,
m is 0; and
$R^2$ represents:
- a phenyl group optionally substituted by at least a substituent chosen among an $C_1$-$C_6$ alkyl group, linear or branched, or a O—($C_1$-$C_6$)-alkyl group, linear or branched, preferably a O—($C_1$-$C_3$)-alkyl group, linear or branched; or
- a 6-membered heteroaryl group, preferably comprising at least one nitrogen, preferably pyridine.

Preferably, in the compounds of the invention,
m is 0; and
$R^2$ represents:
- a 6-membered heteroaryl group, preferably comprising at least one nitrogen, preferably pyridine.

Preferably, in the compounds of the invention,
$R^1$ is —C(O)CH$_2$CH$_2$C(O)OH; and
$R^2$ represents:
- a phenyl group optionally substituted by at least a substituent chosen among an $C_1$-$C_6$ alkyl group, linear or branched, or a O—($C_1$-$C_6$)-alkyl group, linear or branched, preferably a O—($C_1$-$C_3$)-alkyl group, linear or branched; or
- a 6-membered heteroaryl group, preferably comprising at least one nitrogen, preferably pyridine.

Preferably, in the compounds of the invention,
$R^1$ is —C(O)CH$_2$CH$_2$C(O)OH; and
$R^2$ represents:
- a 6-membered heteroaryl group, preferably comprising at least one nitrogen, preferably pyridine.

Preferably, in the compounds of the invention,
$R^1$ is —C(O)CH$_2$CH$_2$C(O)OH;
m is 0 and
$R^2$ represents:
- a phenyl group optionally substituted by at least a substituent chosen among an $C_1$-$C_6$ alkyl group, linear or branched, or a O—($C_1$-$C_6$)-alkyl group, linear or branched, preferably a O—($C_1$-$C_3$)-alkyl group, linear or branched; or
- a 6-membered heteroaryl group, preferably comprising at least one nitrogen, preferably pyridine.

Preferably, in the compounds of the invention,
$R^1$ is —C(O)CH$_2$CH$_2$C(O)OH;
m is 0 and
$R^2$ represents:
- a 6-membered heteroaryl group, preferably comprising at least one nitrogen, preferably pyridine.

The compounds according to the invention can be synthetized as mentioned in WO2012/17515 and WO2012/175707, incorporated herein by reference.

The compounds of formula (I) have a carboxylic function and may be salified. They may then be in the form of addition salts with organic or mineral bases. The addition salts with bases are for example pharmaceutically acceptable salts such as sodium salts, potassium salts or calcium salts, which are obtained using corresponding alkaline-metal and alkaline-earth metal hydroxides as bases. As another type of addition salt with pharmaceutically acceptable bases, mention can be made of the salts with amines and in particular glucamine, N methylglucamine, N,N-dimethylglucamine, ethanolamine, morpholine, N methylmorpholine or lysine.

The compounds of formula (I) may also be salified with mineral or organic acids and preferably pharmaceutical acids such as hydrochloric, phosphoric, fumaric, citric, oxalic, sulphuric, ascorbic, tartric, maleic, mandelic, methanesulphonic, lactobionic, gluconic, glucaric, succinic, sulfonic or hydroxypropane sulfonic acids.

The compounds of the present invention are useful for treating or preventing, preferably treating, NASH.

The present invention also concerns pharmaceutical compositions comprising by way of active principle at least one compound according to the invention for use for the prevention or treatment, preferably treatment, of NASH. These compositions may also comprise a pharmaceutically acceptable vehicle and/or excipient.

The pharmaceutical compositions may be in any forms known to persons skilled in the art, in particular in the forms intended for administration by parenteral, oral, rectal, permucosal or percutaneous method, preferably orally.

The compositions according to the invention will be presented in the form of injectable solutes or suspensions or multi-dose flasks, in the form of bare or coated tablets, pills, capsules, powders, suppositories or rectal capsules, solutions or suspensions, for percutaneous use, in a polar solvent, or permucosal use.

The excipients that are suitable for such administrations are derivatives of cellulose or microcrystalline cellulose, alkaline-earth carbonates, magnesium phosphate, starches, modified starches or lactose for solid forms.

For rectal use, cocoa butter or polyethylene glycol stearates are the preferred excipients.

For parenteral use, water, aqueous solutes, physiological serum and isotonic solutes are the vehicles most conveniently used.

The posology may vary within large limits according to the therapeutic indication and the administration method, as well as the age and weight of the subject.

The invention also concerns a method of preventing or treating, preferably treating, NASH, comprising the administration, to a patient who so requires, of a sufficient quantity of at least one compound according to the invention with a pharmaceutically acceptable vehicle or excipient.

The identification of the patient who needs the treatment indicated above is defined by a person skilled in the art. A veterinary or a doctor may identify, by means of clinical tests, physical examination, biological tests or diagnoses and by the family and/or medical history, the subjects who need such a treatment.

Sufficient quantity means a quantity of compound according to the present invention effective for preventing or treating pathological conditions. The sufficient quantity may be determined by a person skilled in the art, by means of conventional technology and by the observation of the results obtained in similar circumstances. To determine the sufficient quantity, various factors must be taken into account by a person skilled in the art, in particular and without being limited thereto: the subject, his size, his age, his general state of health, the illness involved and the degree of severity thereof; the response of the subject, the type of compound, the administration method, the bioavailability of the composition administered, the dosage, the concomitant use of other medications, etc. Preferably, 5 to 500 mg/day of the compound according to the invention is administered to the patient in one or more doses, preferably in one dose.

The present invention also concerns a method of preventing or treating, preferably treating, NASH, comprising the administration, to a patient who needs it, of a sufficient quantity of at least one composition according to the invention.

The present invention also concerns the use of the compounds of formula (I) for the preparation of a medication for the prevention or treatment, preferably treatment, of NASH.

The present invention also concerns the use of the composition according to the invention for the preparation of a medication for the prevention or treatment, preferably treatment, of NASH.

In addition to the treatment of NASH, the compounds according to the invention are also useful for the treatment of fibrosis, preferably liver fibrosis. Indeed, the present invention also relates to the compounds according to the invention for use for the prevention or treatment, preferably treatment of fibrosis, preferably liver fibrosis. The present invention also relates to the composition according to the invention for use for the prevention or treatment, preferably treatment of fibrosis, preferably liver fibrosis.

The present invention also relates to a method of preventing or treating, preferably treating, fibrosis, preferably liver fibrosis, comprising the administration, to a patient who so requires, of a sufficient quantity of at least one compound or a composition according to the invention with a pharmaceutically acceptable vehicle or excipient.

The present invention also concerns the use of the compounds or composition according to the invention for the preparation of a medication for the prevention or treatment, preferably treatment, of fibrosis, preferably liver fibrosis.

The present invention also relates to the compounds according to the invention for use for the prevention or treatment, preferably treatment, of NASH and fibrosis, preferably liver fibrosis. The present invention also relates to the composition according to the invention for use for the prevention or treatment, preferably treatment, of NASH and fibrosis, preferably liver fibrosis.

The present invention also relates to a method of preventing or treating, preferably treating, NASH and fibrosis, preferably liver fibrosis, comprising the administration, to a patient who so requires, of a sufficient quantity of at least one compound or a composition according to the invention with a pharmaceutically acceptable vehicle or excipient.

The present invention also concerns the use of the compounds or composition according to the invention for the preparation of a medication for the prevention or treatment, preferably treatment, of NASH and fibrosis, preferably liver fibrosis.

The present invention will now be described with the help of non-limitative examples.

The following compound (1) of formula (I) has been tested:

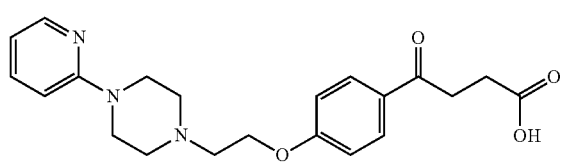 [SMILES: O=C(O)CCC(=O)c1ccc(OCCN2CCN(c3ccccn3)CC2)cc1]

This compound is obtained as described in WO 2012/175715.

The study was made on STAM model.

Pathogen-free fourteen day-pregnant C57BL/6 mice have been obtained from Japan SLC, Inc. (Japan). NASH has been established in male mice by a single subcutaneous injection of streptozotocin (Sigma, USA) after birth and feeding with a high fat diet (CLEA Japan, Japan) ad libitum after four weeks of age (day 28±2). Mice have been randomized into three groups of ten mice at six weeks of age (day 42±2), and three groups of ten mice at nine weeks of age (day 63±2), in the days before the start of treatment. Individual body weights have been measured daily during the treatment period. Food consumption has been measured twice per week during the treatment period. Survival, clinical signs and behavior of mice have been monitored daily.

In Vivo Study 1 to Assess Effects on NASH

The NASH in vivo study had 3 arms:

Group 1 (Vehicle): Ten NASH mice have been orally administered the same vehicle (0.5% methyl cellulose in water) as the mice receiving compound (1).

Group 2 (Telmisartan): Five mice have been administered the same vehicle supplemented with Telmisartan at a dose of 100 mg/kg (in 0.5% methyl cellulose in water) once daily from six to nine (6 to 9) weeks of age. Telmisartan, an angiotensin receptor blocker, is the reference compound which has been shown to be active to treat NASH and fibrosis in the STAM animal model.

Group 3 (compound (1)): Ten NASH mice have be orally administered vehicle supplemented with compound (1) at a dose of 100 mg/kg (in 0.5% methyl cellulose in water) once daily from six to nine (6 to 9) weeks of age. The assessed parameters and histological outcome measures are described below.

In Vivo Study 2 to Assess Effects on Fibrosis

The fibrosis in vivo study had 3 arms:

Group 1 (Vehicle): Ten NASH mice have been orally administered the same vehicle (0.5% methyl cellulose in water) as the mice receiving compound (1).

Group 2 (Telmisartan): Five mice have been administered the same vehicle supplemented with Telmisartan at a dose of 100 mg/kg (in 0.5% methyl cellulose in water) once daily from nine to twelve (9 to 12) weeks of age.

Group 3 (compound (1)): Ten NASH mice have been orally administered vehicle supplemented with compound (1) at a dose of 100 mg/kg (in 0.5% methyl cellulose in water) once daily from nine to twelve (9 to 12) weeks of age. The assessed parameters and histological outcome measures are described below.

Study Measures, Analytes, Outcomes and Analyses

The following measurements have been conducted for both in vivo studies:
- Individual liver weight
- Individual body weight
- Plasma ALT (Alanine AminoTransferase), AST (Aspartate AminoTransferase), triglyceride, and total cholesterol have been measured by FUJI DRI-CHEM (Fujifilm, Japan)
- Liver triglyceride has been quantified by Triglyceride E-test kit (Wako, Japan)
- Histological analyses for liver sections (according to routine methods)
- HE (Hematoxylin Eosin) staining and estimation of NAFLD Activity score (NAS)

Definition and Calculation of NAS

The NAFLD activity score (NAS), proposed by the NASH Clinical Research Network, is the most widely used scoring system in the field of NAFLD/NASH research (Kleiner, D E., et al., (2005). Design and validation of a histological scoring system for nonalcoholic fatty liver disease. Hepatology, 41, 1313-21).

NAS is defined as the unweighted sum of the histological scores for steatosis (0-3), lobular inflammation (0-3) and hepatocyte ballooning (0-2) (see Table), which represent active liver injury. NAS yields a total score from 0 to 8 and allows detailed analysis of histological changes for comparative and correlative studies in clinical and non-clinical trials.

NAS was originally developed for evaluation, but not for diagnosis of NAFLD/NASH.

Nevertheless, the score has been frequently used for NASH diagnosis, with the NAS of 5 considered as a threshold. Although NAS shows good correlation with the diagnosis, careful interpretation must be required. There are the cases where non-NASH livers may score the total NAS of ≥5, or on the contrary, livers with NAS≤4 may receive a diagnosis of NASH (Brunt, E M., et al., (2011). Nonalcoholic fatty liver disease (NAFLD) activity score and the histopathologic diagnosis in NAFLD: distinct clinicopathologic meanings. Hepatology, 53, 810-20 and Hjelkrem, M., et al., (2011). Validation of the non-alcoholic fatty liver disease activity score. Aliment. Pharmacol. Ther., 34, 214-8).

In case of evaluation of drug efficacy, NAS is useful when applied strictly to histologically proven NASH patients. From the aspect of non-clinical studies, NAS should be carefully used when applied to animal model of uneven onset of NASH pathology.

Since Stelic's proprietary NASH-HCC model (STAM model) has uniform and reproducible [100%] disease progression, the STAM model is favorable for comparative studies using NAS.

A network established in 2002 by the National Institute of Diabetes and Digestive and Kidney Diseases (NIDDK) to study the natural history of and conduct clinical trials for adult and pediatric fatty liver disease.

Definition of NAS Components

TABLE 1

Components of NAFLD Activity score (adapted from Kleiner et al., 2005)

| Item | score | Extent |
| --- | --- | --- |
| Steatosis | 0 | <5% |
|  | 1 | 5-33% |
|  | 2 | >33-66% |
|  | 3 | >66% |
| Hepatocyle Balooning | 0 | None |
|  | 1 | Few balloon cells |
|  | 2 | Many cells/prominent ballooning |
| Lobular Inflammation | 0 | No foci |
|  | 1 | <2 foci/200x |
|  | 2 | 2-4 foci/200x |
|  | 3 | >4 foci/200x |

The results are given in the figures enclosed.

FIG. 1 represents the NAS score for study 1 and 2 for each group 1 (vehicule), 2 (Telmisartan) and 3 (compound according to the invention).

Figure 2:
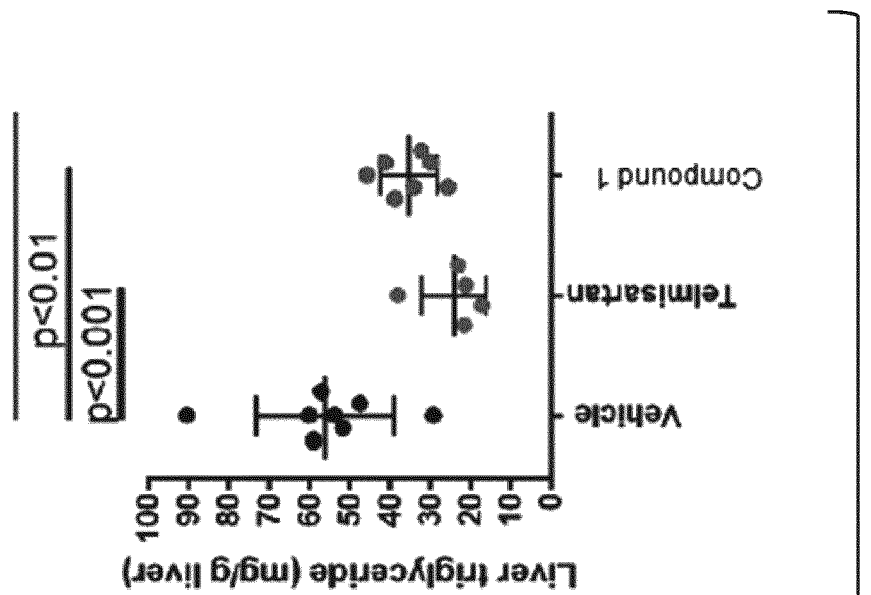
Figure 2:
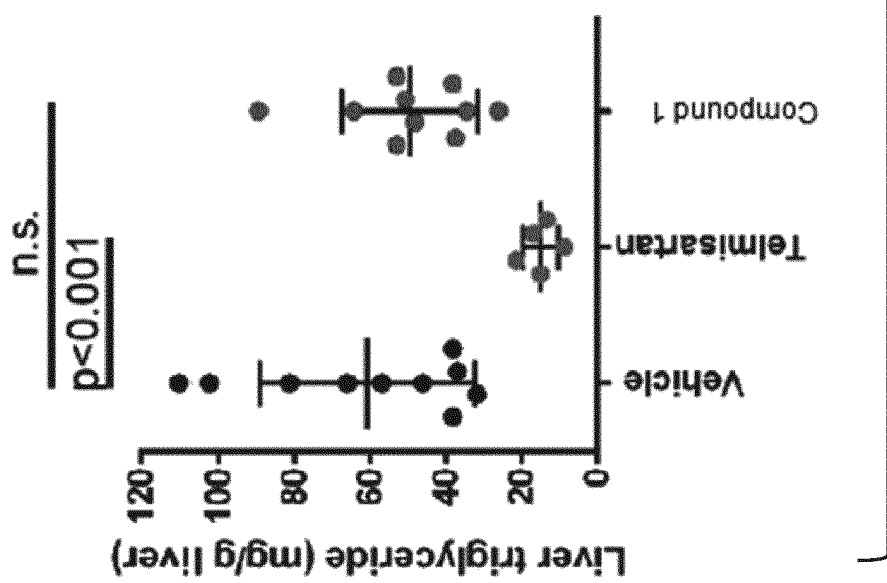

FIG. 2 shows the amount of triglycerides in liver for study 1 and 2 for each group 1 (vehicule), 2 (Telmisartan) and 3 (compound according to the invention).

Figure 3:
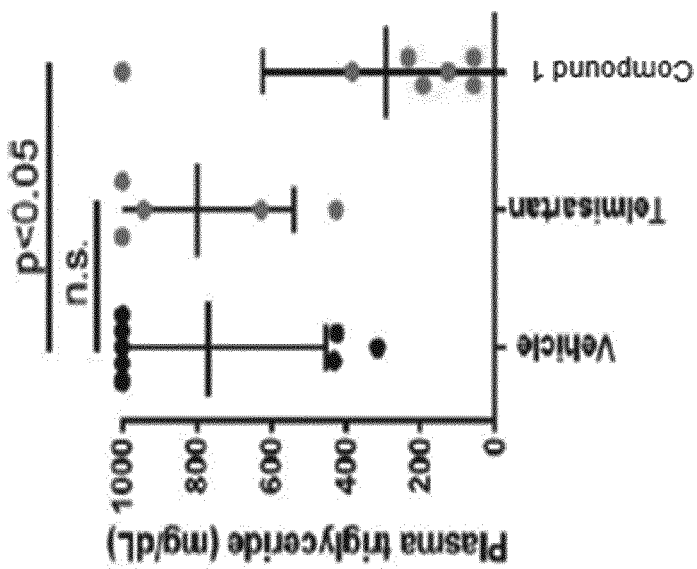
Figure 3:
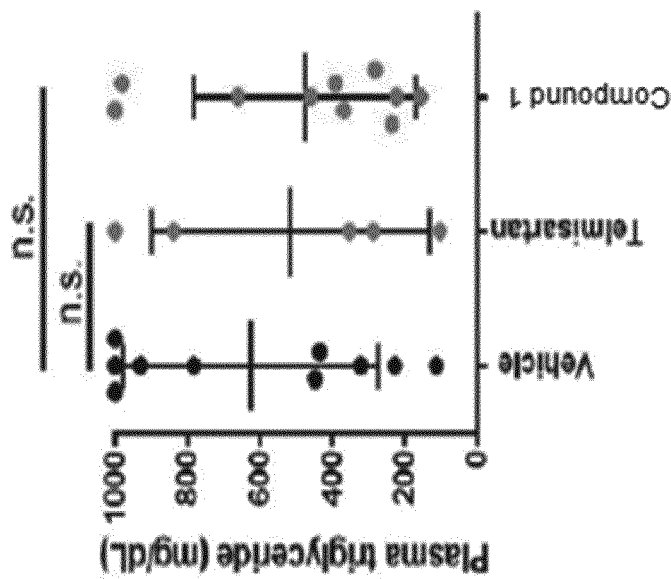

FIG. 3 shows the amount of triglycerides in plasma for study 1 and 2 for each group 1 (vehicule), 2 (Telmisartan) and 3 (compound according to the invention).

Compound (1) according to the invention shows significant reduction in NAFLD activity score (NAS) in both study 1 and 2 in comparison to both vehicle and Telmisartan.

Compound (1) according to the invention shows a reduction in the amount of liver triglycerides (TG).

Compound (1) according to the invention shows a reduction in the amount of plasma triglycerides (TG) especially in study 2.

The invention claimed is:

1. A method for the treatment of NASH comprising the administration to a person in need thereof of a therapeutically effective amount of a compound of formula (I):

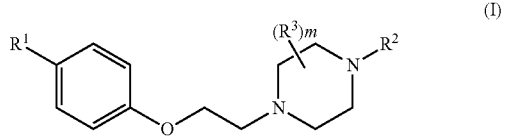

wherein
R¹ represents:
  a group —C(O)CR⁴R⁵CR⁶R⁷C(O)OH; or
  a —(CH₂)₄C(O)OH group;
m represents an integer ranging from 0 to 8;
R² represents:
  a C₆ to C₁₀ aryl group optionally substituted; or
  5 to 10-membered heteroaryl group optionally substituted;
R³, identical or different, represent:
  an alkyl, linear or branched, C₁ to C₅; optionally substituted by a carbocycle group or by a heterocycle group, the carbocycle being in 5 to 10 members, saturated, partially unsaturated or aromatic, substituted or non-substituted, the heterocycle comprising 5 to 10 members, substituted or non-substituted, saturated, partially unsaturated or aromatic and which may comprise 1, 2 or 3 heteroatoms, identical or different,
R⁴, R⁵, R⁶ and R⁷, identical or different, represent:
  a hydrogen atom;
  an alkyl group, linear or branched, in C₁ to C₅;
  a 5, 6 or 7-membered carbocycle group saturated, partially insaturated or aromatic, non-substituted or substituted; or
R⁴ and R⁵ form together with the carbon atom to which they are bonded a carbocycle with 5, 6 or 7 members, substituted or non-substituted; or
R⁶ and R⁷ form together with the carbon atom to which they are bonded a carbocycle with 5, 6 or 7 members, substituted or non-substituted;
or their enantiomers, diastereoisomers thereof and the addition salts thereof with pharmaceutically acceptable bases or acids.

2. The method according to claim 1 wherein m is 0.

3. The method according to claim 1 wherein R¹ is —C(O)CH₂CH₂C(O)OH.

4. The method according to claim 1 wherein R² represents:
  a C₆ to C₁₀ aryl group optionally substituted by at least a substituent selected from the group consisting of an C₁-C₆ alkyl group, linear or branched, and a O—(C₁-C₆)-alkyl group, linear or branched, or
  a 5 to 10-membered heteroaryl group.

5. The method according to claim 1 wherein R² represents a 5 to 10-membered heteroaryl group.

6. The method according to claim 1 wherein R² represents a 6-membered heteroaryl group.

7. The method for the treatment of NASH according to claim 1 wherein the compound is in the form of a pharmaceutically acceptable composition.

8. The method for the treatment of fibrosis, comprising the administration to a person in need thereof of a therapeutically effective amount of a compound of formula (I):

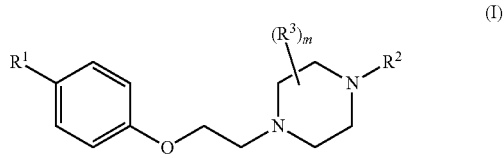

wherein
R¹ represents:
  a group —C(O)CR⁴R⁵CR⁶R⁷C(O)OH; or
  a —(CH₂)₄C(O)OH group;
m represents an integer ranging from 0 to 8;
R² represents:
  C₆ to C₁₀ aryl group optionally substituted; or
  a 5 to 10-membered heteroaryl group optionally substituted;
R³, identical or different, represent:
  an alkyl, linear or branched, C₁ to C₅; optionally substituted by a carbocycle group or by a heterocycle group, the carbocycle being in 5 to 10 members, saturated, partially unsaturated or aromatic, substituted or non-substituted, the heterocycle comprising 5 to 10 members, substituted or non-substituted, saturated, partially unsaturated or aromatic and which may comprise 1, 2 or 3 heteroatoms, identical or different,
R⁴, R⁵, R⁶ and R⁷, identical or different, represent:
  a hydrogen atom;
  an alkyl group, linear or branched, in C₁ to C₅;
  a 5, 6 or 7-membered carbocycle group saturated, partially unsaturated or aromatic, non-substituted or substituted; or
R⁴ and R⁵ form together with the carbon atom to which they are bonded a carbocycle with 5, 6 or 7 members, substituted or non-substituted; or
R⁶ and R⁷ form together with the carbon atom to which they are bonded a carbocycle with 5, 6 or 7 members, substituted or non-substituted;
or their enantiomers, diastereoisomers thereof and the addition salts thereof with pharmaceutically acceptable bases or acids.

9. The method for the treatment of fibrosis according to claim 8, wherein the compound is in the form of a pharmaceutically acceptable composition.

10. The method according to claim 1 wherein the fibrosis is liver fibrosis.

11. A method for the treatment of NASH comprising the administration to a person in need thereof of a therapeutically effective amount of a compound of formula (I):

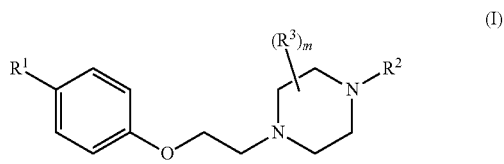

wherein
R¹ represents:
  a group —C(O)CR⁴R⁵CR⁵R⁷C(O)OH; or
  a —(CH₂)₄C(O)OH group;
m represents an integer ranging from 0 to 8;
R² represents:
  a $C_6$ to $C_{10}$ aryl group optionally substituted; or
  a 5 to 10-membered heteroaryl group optionally substituted;
R³, identical or different, represent:
  an alkyl, linear or branched, $C_1$ to $C_5$, optionally substituted by a carbocycle group or by a heterocycle group, the carbocycle being in 5 to 10 members, saturated, partially unsaturated or aromatic, substituted or non-substituted, the heterocycle comprising 5 to 10 members, substituted or non-substituted, saturated, partially unsaturated or aromatic and which may comprise 1, 2 or 3 heteroatoms, identical or different;
R⁴, R⁵, R⁶ and R⁷, identical or different, represent:
  a hydrogen atom;
  an alkyl group, linear or branched, in $C_1$ to $C_5$;
  a 5, 6 or 7-membered carbocycle group saturated, partially unsaturated or aromatic, non-substituted or substituted; or
R⁴ and R⁵ form together with the carbon atom to which they are bonded a carbocycle with 5, 6 or 7 members, substituted or non-substituted; or
R⁶ and R⁷ form together with the carbon atom to which they are bonded a carbocycle with 5, 6 or 7 members, substituted or non-substituted;
or their enantiomers, diastereoisomers thereof and the addition salts thereof with pharmaceutically acceptable bases or acids.

12. A method for the treatment of fibrosis comprising the administration to a person in need thereof of a therapeutically effective amount of a compound of formula (I):

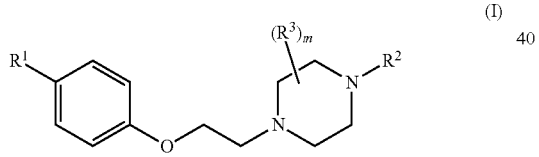

(I)

wherein
R¹ represents:
  a group —C(O)CR⁴R⁵CR⁶R⁷C(O)OH; or
  a —(CH₂)₄C(O)OH group;
m represents an integer ranging from 0 to 8;
R² represents:
  a $C_6$ to $C_{10}$ aryl group optionally substituted; or
  a 5 to 10-membered heteroaryl group optionally substituted;
R³, identical or different, represent:
  an alkyl, linear or branched, $C_1$ to $C_5$; optionally substituted by a carbocycle group or by a heterocycle group, the carbocycle being in 5 to 10 members, saturated, partially unsaturated or aromatic, substituted or non-substituted, the heterocycle comprising 5 to 10 members, substituted or non-substituted, saturated, partially unsaturated or aromatic and which may comprise 1, 2 or 3 heteroatoms, identical or different,
R⁴, R⁵, R⁶ and R⁷, identical or different, represent:
  a hydrogen atom;
  an alkyl group, linear or branched, in $C_1$ to $C_5$;
  a 5, 6 or 7-membered carbocycle group saturated, partially unsaturated or aromatic, non-substituted or substituted; or
R⁴ and R⁵ form together with the carbon atom to which they are bonded a carbocycle with 5, 6 or 7 members, substituted or non-substituted; or
R⁶ and R⁷ form together with the carbon atom to which they are bonded a carbocycle with 5, 6 or 7 members, substituted or non-substituted;
or their enantiomers, diastereoisomers thereof and the addition salts thereof with pharmaceutically acceptable bases or acids.

13. The method according to claim 12 wherein the fibrosis is liver fibrosis.

* * * * *